United States Patent [19]

Mossholder

[11] Patent Number: Plant 7,457

[45] Date of Patent: Feb. 26, 1991

[54] AZALEA HYBRID 'JESSICA DAWN'

[75] Inventor: Rose M. Mossholder, Fallbrook, Calif.

[73] Assignee: Hines Nurseries Inc., Irvine, Calif.

[21] Appl. No.: 351,138

[22] Filed: May 12, 1989

[51] Int. Cl.[5] ..... A01H 5/00

[52] U.S. Cl. ..... Plt./56

[58] Field of Search ..... Plt./55-57

[56] References Cited

PUBLICATIONS

Galle, Fred C., "List of Registered Azaleas", *Azaleas Revised and Enlarged Edition,* Date & Publisher unknown, pp. 445, 447, 97, 98, 192, 193, 236, 237, 243, 281, and 282.

Leach, D. G., (Listing) 'Jessica' *Rhododendrons of the World,* Charles Schribner's Sons, N.Y., 1961, p. 461.

*Primary Examiner*—James R. Feyrer

[57] ABSTRACT

The new plant is a hybrid evergreen azalea characterized by a compact horizontally spreading form with ascending branches, a uniform, strong and vigorous rooting habit, and blooms which appear in clusters of two to four. The azalea blooms mid-season (early March–April) in Irvine, Calif. Blooms have a diameter of about 7.6 to 8.9 cm, a double hose-in-hose open funnel shaped form with petaloid stamens, and petals with an upper surface marbled in four shades of pink.

4 Drawing Sheets

BACKGROUND OF THE INVENTION

The present invention relates to a new and distinct variety of evergreen azalea of the genus Rhododendron and a member of the Ericaceae family. This new variety of azalea plant is the result of a breeding program. The principal objectives of this breeding program were to produce new varieties of evergreen azaleas which are floriferous, compact, vigorous, and easy to propagate using vegetative cuttings.

The specific parentage of the new variety is unknown because no records were kept of the crosses which resulted in the new plant. The breeding program incorporated the use of forty seven varieties of evergreen azalea from seven hybrid groups that were grown at Mossholder Nurseries in La Habra, Calif.

Hybrid Groups Used in the Breeding Program

| | # of Cultivars |
|---|---|
| Belgian Indian Hybrids | 25 |
| Coolidge Hybrids | 3 |
| Mossholder-Bristow Hybrids | 11 |
| Pericat Hybrids | 2 |
| Rutherford Hybrids | 2 |
| Southern Indian Hybrids | 1 |
| Kurume Hybrids | 3 |

'Jessica Dawn' most closely resembles the Mossholder-Bristow and the Belgian Indian Hybrid groups.

This new hybrid has the following combination of characteristics which distinguish it from other varieties.

1. Flower size, color, form and season of bloom: The large 7.6 to 8.9 cm blooms are double and marbled with four shades of pink. Petal margins are ruffled. Blooms mid-season (early March–April).
2. Plant form and vigor: The plant is compact, horizontally spreading and very vigorous.
3. Ease of vegatative propagation by softwood cuttings: The new hybrid has been asexually reproduced thousands of times by rooting cuttings at Hines Nursery in Irvine, Calif. Each of the progeny exhibits identical characteristics of the mother plant, establishing the hybrid as reproducible and true to type.

DESCRIPTION OF THE PHOTOGRAPHS

DETAILED PLANT DESCRIPTION

The following is a detailed description of the new hybrid azalea plant based on not less than 15 specimens for each specific characteristic. Color determinantions and comparisons are all based on The Royal Horticultural Society Colour Chart.

Origin: Hybrid seedling.

Parentage: Unknown.

Classification: Hybrid.

Form: Globose.

Habit: Dense and twiggy (compact), with horizontally spreading and ascending branches. Position of the branches are whorled. As plant matures, the width becomes greater than the height.

Plant vigor: Active, strong, rapid growth on the plant's own rootstock (vigorous). Estimated annual terminal growth about 17–18 cm.

Figure 1:
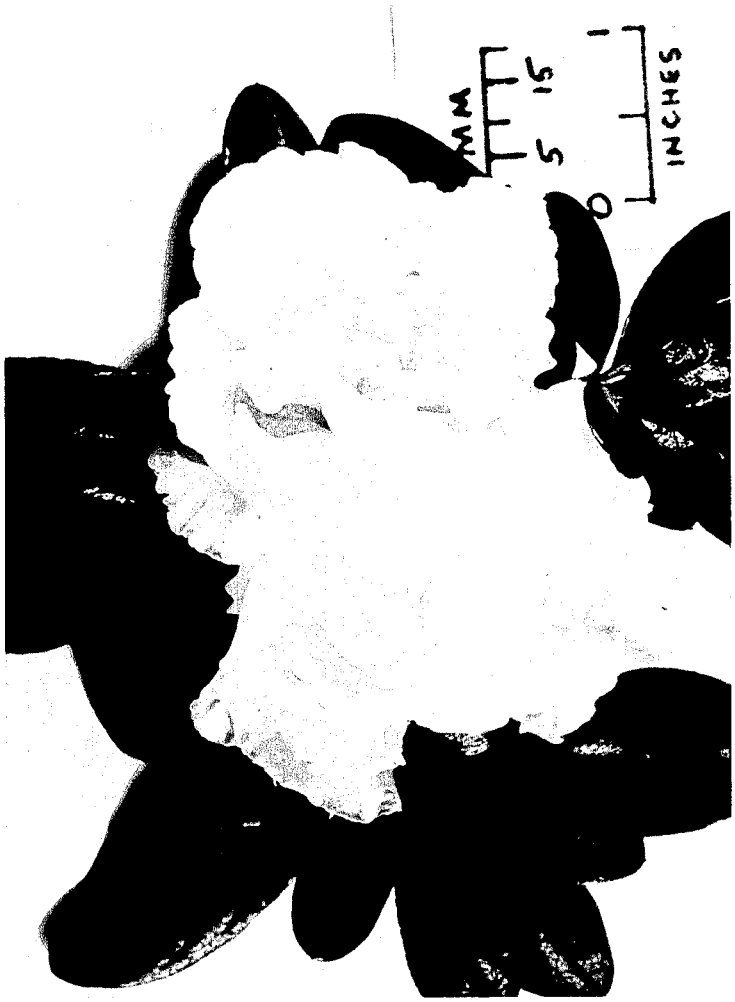
FIG. 1 is a close-up showing flower color, size and form.
Figure 2:
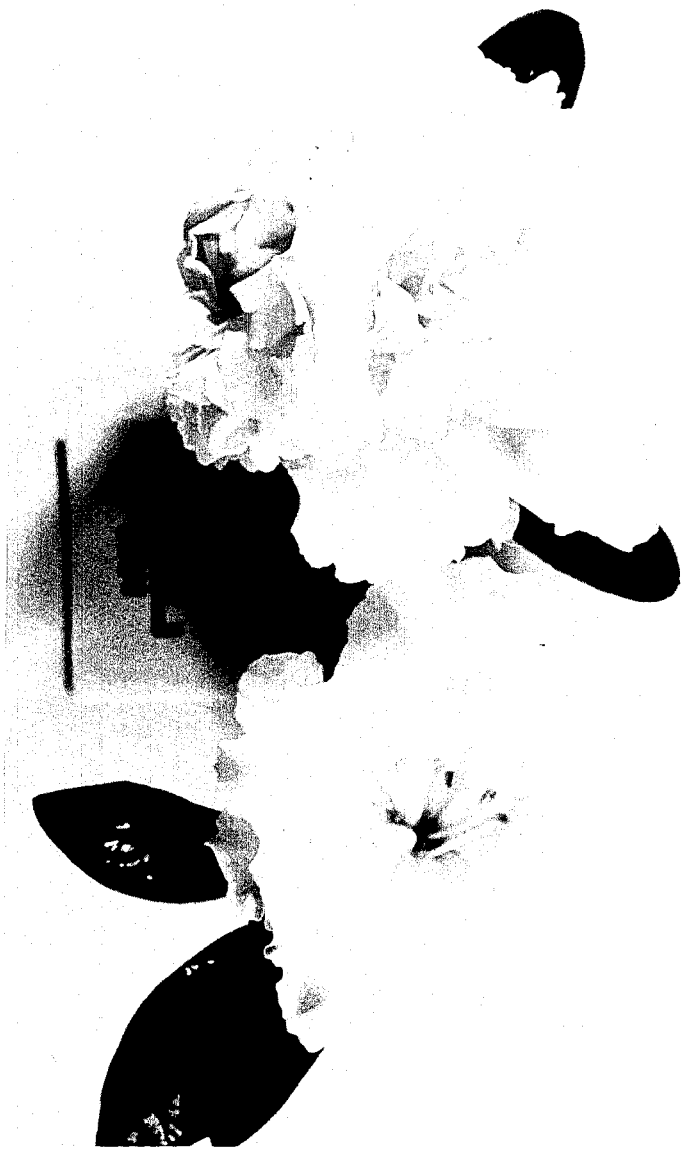
FIG. 2 is a comparison of 'Jessica Dawn' blossom (right) and 'Easter Parade' blossom (left).
Figure 3:
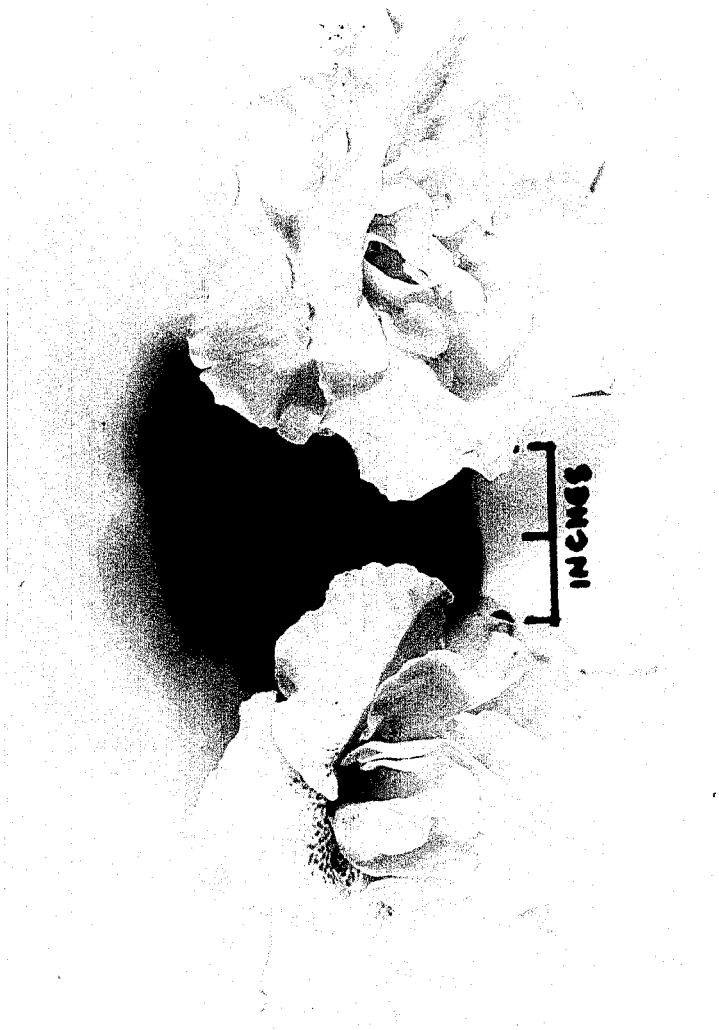
FIG. 3 is a comparison of 'Jessica Dawn' blossom (right) and 'Pink Pearl' blossom (left).
Figure 4:
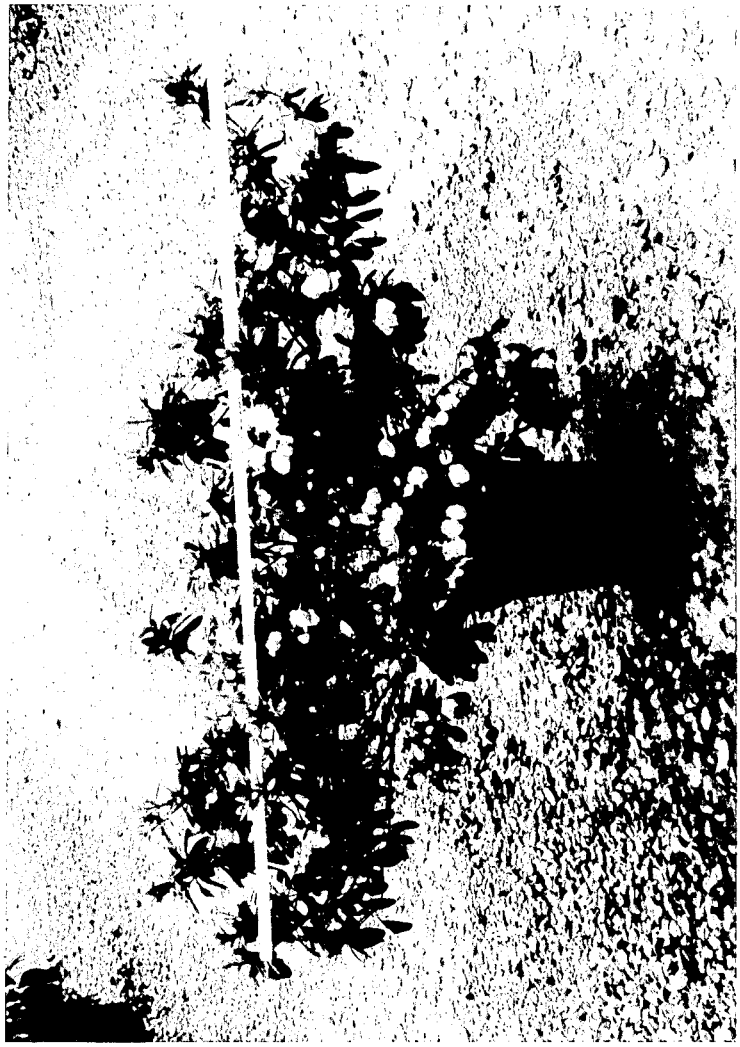
FIG. 4 is a photograph of a four year old plant displaying the overall habit.

Size: Height of a 9 year old plant in a #15 container reached 99 cm (39 inches). The width was not considered normal since the plant was somewhat cramped for space FIG. 4 shows a 4 year old plant with branches spreading horizontally 90 cm (35 inches) and with a height of 66 cm (20 inches). Other plants given adequate space and with minimal pruning exhibited this same spreading habit. Estimated height for a mature plant (10 years) is approximately 90–102 cm (35–40 inches) with a spread of 91–152 cm (36–60 inches).

Blooming habit: Prolific.

Blooming period: Blooms appear in early March and continue to bloom through mid-April in Irvine, Calif.

Rooting: Very uniform; strong and vigorous.

HARDINESS

Minimum temperature range for 'Jessica Dawn' is normally −7° C. to −1° C. (20°–30° F.). Minor frost damage occurred to newly formed foliage and flower buds during a February cold spell in Irvine, Calif. when the temperature reached a minimum of −3° C. (26° F.). The plant has not been tested for maximum hardiness.

FOLIAGE

Arrangement: Opposite and whorled.

Type: Evergreen.

Shape: Oblanceolate, obtuse, cuneate, flat.

Size:

*Average length of mature foliage (from petiole to leaf apex).*—6.7 cm.

*Average width of mature foliage.*—2.5 cm.

Color:

*Upper surface.*—Fan 3, Yellow-Green Group No. 147A.

*Lower surface.*—Fan 3, Yellow-Green Group No. 146B.

Margins: Entire, ciliate.

Texture: Glossy, coarse, strigose. Color of indumentum on young leaves: Yellow-White Group 158A to 164B. Color of indumentum on mature leaves: Grey-Orange Group 163A to 164A.

Petiole: Average length 0.8 cm, Yellow-Green Group 145A.

Buds: Elliptic, Yellow-Green Group 144B to 144C with white sericeous hairs.

Stems: Young growth Yellow-Green Group 144B matures to Grey-Orange Group 166C; strigose, hair color Grey-Orange Group 166B.

BUDS

Flower buds: At approximate age 2 weeks buds were stil tight but beginning to unfold at apex. Buds were broadly ovate and obtuse with a length of 2.6 cm and a diameter of about 1.1 cm. The color is not significantly different from mature flowers.

Calyx: Non-persistent, broadly ovate, obtuse, imbricated, Yellow-Green Group 144B to 144D with sericeous, copper brown, Grey-Orange Group 167A, hairs at the apex of each sepal.

INFLORESCENCE

Flower: Incomplete and perfect, sepals fall off as buds open.

Blooming period: Blooms appear in early March and continue through mid-April in Irvine, Calif.

How borne: In clusters of two to four.

Size: Medium large, 7.6 to 8.9 cm in diameter and 4.0 to 5.0 cm in length.

Petalage:

*Color.*—Upper surface of the petals are marbled with four shades of pink, Fan 1, Red Group 49A, B, C, and D. Throat is dotted with a shade of chartreuse, Fan 3, Yellow-Green Group 153C.

*Form.*—10 lobes fused at base with 5–7 petaloid stamens, connate.

*Pedicel.*—Length 0.8 cm. Yellow-Green Group 145B, C with whitish sericeous hairs.

*Shape.*—Rounded.

*Margin.*—Sinuate (ruffled).

*Texture.*—Smooth, satiny.

*Persistence.*—Petals hang and dry, turn various shades of brown, discolored, with age.

*Fragrance.*—None.

Form: Double hose-in-hose with petaloid stamens. Openly funnel-shaped.

Reproductive organs:

*Stamens.*—Average 5 to 7, variable, petaloid with greenish-white anthers. White pollen present but not tested for viability.

*Pistils.*—Single, average length 2.3 cm, slightly shorter than petal length. Colors of style and stigma range from Yellow-Green Group 153C to Red Group 49A–D depending on age.

*Ovary.*—Five locules within a hypogynous ovary enclosed by a sericeous ovary wall. Seeds observed to form but not tested for viability.

Disease resistance: Normal as compared with other azalea varieties grown under the same cultural conditions at Irvine, Calif.

DESCRIPTION OF MOST SIMILAR AZALEA CULTIVARS

Azalea 'Jessica Dawn' has large 7.6 to 8.9 cm blooms that are double and marbled with four shades of pink and with ruffled margins. The plant blooms mid-season (early March to mid-April in California). The following cultivars represent those most similar to 'Jessica Dawn' that the inventor is aware of in the nursery trade.

'Easter Parade': Single hose-in-hose, 7.6 cm, pink blooms with white marbling. Chartreuse flecks in the throat. Late season bloomer.

'Pink Pearl': Double, 5.1 cm, phlox pink blooms with red-purple flecks in throat. Mid to late season bloomer.

'Pink Lady': Double, light coral pink with salmon flecks. Sport of 'Eric Shame'.

'California Pink Dawn': Double, 7.6 cm blooms are blush pink with dark pink flecks. Blooms early to mid-season. Sport of 'California Sunset'.

'Califronia Sunset': Double, 7.6 cm blooms are deep pink edged with white, early to mid season.

Of the plants used in the breeding program 'Easter Parade' and 'Pink Pearl' were the most similar to the new selection. Of the other commercially available plants known to the inventor 'Pink Lady', 'California Pink Dawn', and 'California Sunset' are the most similar.

REFERENCES

Galle, F. 1987 *Azaleas,* Rev. Ed., Timber Press, Portland, Oreg.

Hines Nurseries, 1989 *Nursery Catalog,* Irvine, Calif.

Kofranek, A. and R. Larson 1975 *Growing Azaleas Commercially,* The University of California Extension Program.

Melfeld's Nursery, Inc. 1987 *Nursery Catalog,* Riverside, Calif.

Nuccio's Nurseries, 1988–89 *Nursery Catalog,* Altadena, Calif.

I claim:

1. A new variety of hybrid evergreen azalea plant as described and illustrated, characterized by a compact horizontally spreading form with ascending branches, a uniform, strong and vigorous rooting habit, and blooms which appear in clusters of two to four, is a mid-season bloomer (early March–April) in Irvine, Calif., the blooms having a diameter of about 7.6 to 8.9 cm, a double hose-in-hose open funnel shaped form with petaloid stamens, and petals having an upper surface marbled in four shades of pink.

* * * * *